United States Patent [19]

Stewart et al.

[11] Patent Number: 5,770,684

[45] Date of Patent: Jun. 23, 1998

[54] CATALYST COMPOSITIONS

[75] Inventors: Nevin John Stewart, Guildford; Stephen John Dossett, Aldershot, both of United Kingdom

[73] Assignee: BP Chemicals Limited, London, England

[21] Appl. No.: 696,344

[22] Filed: Aug. 13, 1996

[30] Foreign Application Priority Data

Aug. 21, 1995 [GB] United Kingdom ............... 9517105

[51] Int. Cl.$^6$ .................................................. C08G 67/02
[52] U.S. Cl. ..................... 528/392; 528/367; 556/7; 556/13; 556/136; 556/137; 502/155; 502/162; 502/167
[58] Field of Search ................... 528/392, 367; 556/7, 13, 136, 137; 502/155, 162, 167

[56] References Cited

U.S. PATENT DOCUMENTS 3,694,412  9/1972  Nozaki .

FOREIGN PATENT DOCUMENTS

| 121965 | 10/1984 | European Pat. Off. . |
| 181014 | 5/1986 | European Pat. Off. . |
| 222454 | 5/1987 | European Pat. Off. . |
| 90201531 | 6/1990 | European Pat. Off. . |
| 619335 | 10/1994 | European Pat. Off. . |

OTHER PUBLICATIONS

"Zur Kenntnis der Organophosphorverbindungen XX" (*Phosphorus and Sulfur*; K. Diemert et al.; vol. 15, pp. 155–164; ©1983).

"Synthese und Eigenschaften bifunktioneller Organobromphosphane" (*Chem. Ber.*; K. Diemert et al.; vol. 115, pp. 1947–1955; ©1982).

*Primary Examiner*—Duc Truong
*Attorney, Agent, or Firm*—Fay, Sharpe, Beall, Fagan, Minnich & McKee

[57] ABSTRACT

A catalyst composition prepared by reacting together:
(a) a source of a Group VIII metal,
(b) a bidentate phosphine ligand having at least two phosphorous atoms joined by a bridging group of the formula —$NR^2(CX)NR^2$ where X=O, S or Se, each $R^2$ is the same or different and is a hydrogen or hydrocarbyl group, and
(c) a promoter
is disclosed. The catalyst composition is used for preparing polyketones.

9 Claims, No Drawings

CATALYST COMPOSITIONS

The present invention relates to catalyst compositions and to processes for preparing interpolymers of olefins and carbon monoxide by polymerising a mixture of one or more olefins and carbon monoxide in the presence of such catalyst compositions. In particular, the present invention relates to novel compounds and their use in catalysts for such processes.

The preparation of linear alternating interpolymers of olefins and carbon monoxide having the formula:

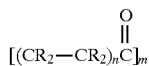

where the R groups are independently hydrogen or hydrocarbyl groups, n is at least 1 and m is a large integer, is known from U.S. Pat. No. 3,694,412. Such linear alternating interpolymers, which hereafter will be called polyketones, are prepared according to U.S. Pat. No. 3,694,412 by polymerising a mixture of one or more olefins and carbon monoxide in the presence of an aryl phosphine complex of a palladium halide and an inert solvent. However, the processes described in U.S. Pat. No. 3,694,412 are slow even at elevated temperature and pressure.

An improved version of the process described in U.S. Pat. No. 3,694,412 is described in European patent applications 181014 and 121965. It was subsequently found that the rate of the polymerisation process could be increased considerably by using a palladium catalyst with inter alia a bidentate phosphine and the anion of a carboxylic acid having a pKa of lower than 2 (as measured in aqueous solution). Examples of anions which can be used include trichloroacetate, dichloroacetate, tetrafluoroborate, hexafluorophosphate and p-toluene sulphonate, such anions being respectively the conjugate anions of trichloroacetic acid, dichloroacetic acid, tetrafluoroboric acid, hexafluorophosphoric acid and p-toluenesulphonic acid.

More recently EP 222454 suggests that any acid having a pKa of less than 5 (determined in aqueous solution at 18° C.) can be used.

It has now been found that instead of using the bidentate diphosphine as described in EP 121965, catalyst systems, in particular palladium catalyst systems, for the production of polyketones based upon novel phosphine ligands can be employed.

According to the present invention there is provided a catalyst composition prepared by reacting together:
(a) a source of a Group VIII metal,
(b) a bidentate phosphine ligand having at least two phosphorus atoms joined by a bridging group of the formula —$NR^2(CX)NR^2$ where X=O, S or Se, each $R^2$ is the same or different and is a hydrogen or hydrocarbyl group, and
(c) a promoter.

The present invention further provides a process for preparing polyketones by polymerising a mixture of carbon monoxide and one or more olefins in the presence of a catalyst composition as defined hereinabove.

The term polyketone is used herein to mean an interpolymer of one or more olefins with carbon monoxide. The idealised structure of such a material would comprise a one, two or three dimensional network of strictly alternating olefin and carbon monoxide units. Although polyketones prepared according to the present invention correspond to this idealised structure, it is envisaged that materials corresponding to this structure in the main but containing small regimes (i.e. up to 10 wt %) of the corresponding polyolefin also fall within the definition.

The catalyst composition described above is itself prepared by reacting together (a) a source of a Group VIII metal, (b) a compound having the formula defined above, and (c) a promoter.

As regards component (a), this is a source of Group VIII metal; the Group VIII metals are iron, cobalt, nickel, ruthenium, rhodium, palladium, osmium, iridium and platinum. The second-row Group VIII metals (i.e. ruthenium, rhodium, palladium) are preferred; particularly preferred is palladium.

Component (b) is a bidentate phosphine ligand having at least two phosphorus atoms joined by a bridging group of the formula —$NR^2(CX)NR^2$ where X=O, S or Se, each $R^2$ is the same or different and is a hydrogen or hydrocarbyl group. In particular component (b) can be a compound of formula I:

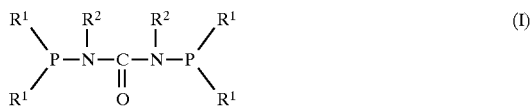

where $R^1$ is hydrocarbyl and $R^2$ is hydrogen or hydrocarbyl, each $R^1$ can be the same or different and each $R^2$ can be the same or different, $R^1$ is a hydrocarbyl group for example an alkyl preferably a $C_1$–$C_6$ alkyl group, alternatively $R^1$ can be an aryl group optionally substituted with a polar group for example phenyl or o methoxy phenyl. The hydrocarbyl group can be a substituted or unsubstituted hydrocarbyl group. $R^2$ on the other hand is hydrogen or a hydrocarbyl group for example a $C_1$–$C_6$ alkyl group for example methyl or ethyl or an aryl group for example phenyl.

In a further aspect of the present invention there is provided a compound of the formula $(Ph_2P)N(Me)CO(Ph)N(PPh_2)$.

As regards component (c) which is a promoter, this can be a source of an anion which is either non-coordinating or weakly coordinating. Such anions are suitably the conjugate bases of strong acids having e.g. a pKa of less than 6 preferably less than 2 (e.g. $HBF_4$, $HPF_6$, $HSbF_6$, paratoluene sulphonic acid). Alternatively, the promoter can be a boron hydrocarbyl compound for example a boron alkyl or boron aryl compound. In particular the Boron hydrocarbyl compound can be a Lewis acid of the formula BXYZ where at least one of X Y and Z is a monovalent hydrocarbyl group. Where any one of X Y or Z is a monovalent hydrocarbyl group, it is suitably an alkyl for example a $C_1$–$C_6$ alkyl group, or an aryl group for example, a substituted or unsubstituted phenyl group for example $C_6H_5$ or $C_6F_5$. Other suitable monovalent hydrocarbyl groups are p-Hal $C_6H_4$ (where Hal=F,Cl,Br), m, m-$C_6H_3(CF_3)_2$, $CF_3$ and $C_2F_5$. It is to be understood that two or three of the groups X, Y and Z can together form bi or trivalent groups respectively. At least one of X, Y and Z is a monovalent hydrocarbyl group; however it is preferred that at least two, preferably three, of X, Y and Z are each monovalent hydrocarbyl groups. Suitable examples of such Lewis acids are $BMe_3$, $BEt_3$, $B(C_6H_5)_3$, $B[mm-(CF_3)_2C_6H_3]_3$, $B(mesityl)_3$, $B(p-Hal\ C_6H_4)_3$ (where Hal=F, Cl, Br), $B(m-CF_3C_6H_4)_3$ and $B(C_6F_5)_3$, preferably $B(p-Hal\ C_6H_4)_3$ and $B(C_6F_5)_3$. Where one or more of X, Y and Z is not a hydrocarbyl group, it is suitably a OH, OR or halide group preferably a halide group for example fluoride, chloride or bromide especially fluoride. Examples of compounds where one of X, Y, Z is a group other than a hydrocarbyl group are boronic acids of the formula RB(OH)$_2$ where R is a hydrocarbyl group e.g. PhB(OH)$_2$, and hydrocarbyl 1,3,2-benzodioxaboroles.

Other suitable boron hydrocarbyl compounds for use in this invention are borate salts of the formula MBR$_4$ where M is an alkali metal e.g. Li, Na, and R is a hydrocarbyl group e.g. C$_6$H$_5$, C$_6$F$_5$ and substituted analogues. For example a suitable compound could be LiB(C$_6$F$_5$)$_4$ or NaB(C$_6$H$_5$)$_4$.

When a boron hydrocarbyl compound is used, for example a Lewis Acid BXYZ it is added to the reaction medium in an amount such that the Group VIII metal: Boron ratio is in the range 10:1 to 1:200 preferably 1:1 to 1:100 more preferably 1:5 to 1:70 e.g. 1:50.

Alternatively, the promoter(c) can be an aluminoxane.

Where the Group VIII metal is palladium, the source of palladium can include simple inorganic and organic salts, e.g. halides, nitrates, carboxylates and the like as well as organometallic and coordination complexes. In some cases, by suitable choice of coordination complex, it may be possible to add the palladium and the compound of formula I as a single entity.

For example the novel compounds of formula II

$$L_2Pd(P-P) \qquad (II)$$

where each L is independently a monodentate ligand or L$_2$ taken together is a bidentate ligand and P—P is a bidentate phosphine ligand having at least two phosphorus atoms joined by a bridging group of the formula —NR$^2$(CO)NR$^2$ where each R$^2$ is the same or different and is a hydrogen or hydrocarbyl group. In particular a compound of the formula II, where R$^1$ and R$^2$ have the meanings assigned to them as hereinabove, can be used together with component (c), a promoter. L in formula II is typically a halide or carboxylate ligand for example CH$_3$COO or CF$_3$COO. In a further aspect of the present invention there are provided compounds of formula II as defined.

Where the promoter is a non-coordinating or weakly coordinating anion, this can also be incorporated into a discrete compound as a counter anion. For example, novel compounds of the formula III can be used

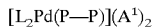

$$[L_2Pd(P-P)](A^1)_2 \qquad (III)$$

where L and P—P have the meanings assigned to them as in formula II above and A$^1$ is a non-coordinating or weakly coordinating anion. L is preferably a 2-electron donor ligand e.g. H$_2$O, ROH (where R is a hydrocarbyl group e.g. Me, Ph), R$_2$CO (where each R is independently a hydrocarbyl group e.g. Me) RCN (where R is an alkyl or aryl group). L is typically benzonitrile or a acetonitrile. An example of a compound of formula III is [(benzonitrile)$_2$Pd(P—P)](BF$_4$)$_2$ where P—P is (Ph$_2$P)N(Me)CO(Ph)N(PPh$_2$).

In a further aspect of the present invention there are provided compounds of the formula III.

Alternatively, the anion can be used in the form of a salt or its conjugate acid together with the Group VIII metal and the compound of formula I whether the latter two are added as a single discrete compound or are added as two components.

Although any source of the Group VIII metal can be used, it may be necessary, when a metal complex having strongly coordinating ligands is employed, to ensure that such ligands are removed. An example of such a complex is palladium acetate where the acetate ligands bind to the palladium. In such cases the acetate ligands can be removed by adding component (c) above for example as the conjugate acid of a non-coordinating or weakly coordinating anion since such a conjugate acid will protonate the acetate ligands and cause their removal.

Another approach which is useful when metal halides e.g. palladium halides are employed (halide anions also bind strongly to the palladium) is to use a thallium or silver salt of a non-coordinating or weakly coordinating anion. In such cases a metathesis reaction occurs and the insoluble silver or thallium halide precipitates and can be removed by filtration.

Considering next the feedstocks for the polymerisation reaction, it is believed that any source of carbon monoxide can be used. Thus the carbon monoxide may contain nitrogen, inert gases and up to 10% hydrogen.

Any olefin can in theory be used although the best reaction rates are obtained when either ethylene or ethylene and at least one other olefin e.g. ethylene/propylene and the like, is used. The lower rates obtained in the absence of ethylene should not be construed as indicating that the process can be used only with an ethylene feedstock since other olefins such as propylene, 4,methylpentene-1, styrene, acrylates, vinyl acetates and the like all undergo reaction to some extent. A preferred polyketone is a terpolymer of ethylene, propylene and carbon monoxide; under these circumstances the olefin will be a mixture of ethylene and propylene.

The catalyst compositions can be used in either the gas-phase or the liquid-phase. It is to be understood that the term liquid phase also includes slurry-phase where the polyketone product is insoluble in the reaction solvent.

Where the polymerisation process is in the liquid phase it is suitably carried out in a solvent which is chemically inert under the conditions employed and one in which the catalyst is soluble. Examples of such solvents include alcohols, e.g. methanol, ethanol and propanol, ethers, glycols, glycol ethers and chlorinated solvents e.g. chloroform and dichloromethane. Preferred solvents are methanol, ethoxyethanol, chloroform or dichloromethane especially dichloromethane. Alternatively, an aliphatic, tertiary alcohol can be used, preferably tertiary butanol. This can be used as a solvent on its own or in combination with an aprotic solvent, e.g. ketones. A preferred solvent system is tertiary butanol/acetone mixture.

The polymerisation process is suitably carried out at a temperature in the range 20° to 150° C. preferably 50° to 120° C. and at elevated pressure (e.g. 1 to 100 bars). The overpressure of gas is suitably carbon monoxide or carbon monoxide and olefin, if the olefin is gaseous under the reaction conditions. It is possible to operate the polymerisation process either batchwise or continuously.

The invention will be illustrated with reference to the following Examples.

EXAMPLE 1

(Ph$_2$P)N(Me)CO(Ph)N(PPh$_2$) was prepared as follows:

PPh$_2$Cl (4.03 g, 18.25 mmol) was added dropwise to a CH$_2$Cl$_2$ solution (20 cm$^3$) of (Me$_3$Si)N(Me)CO(Ph)N (SiMe$_3$) (2.69 g, 9.13 mmol), prepared by a published procedure (Klebe J. F., Bush J. B. and Lyons J. E., J. Am. Chem. Soc. 4401, 1964.), and stirred overnight. The product was precipitated from solution by addition of diethyl ether (50 cm$^3$) and dried in vacuo. The product was further purified by dissolving it in CH$_2$Cl$_2$ (30 cm$^3$) and passing the solution through a silica pad. A further addition of diethyl ether (50 cm$^3$) afforded a precipitate of white microcrystals of (Ph$_2$P)N(Me)CO(Ph)N(PPh$_2$) (3.76 g, 7.30 mmol). $^{31}$P{$^1$H} NMP (CD$_2$Cl$_2$)=53.4 and 48.8 ppm J(AB) 40 Hz.

EXAMPLE 2

(Ph$_2$P)N(H)CO(H)N(PPh$_2$) was prepared as follows:

To a toluene solution (40 cm³) of (Me₃Si)N(H)CO(H)N(SiMe₃) (5.0 g, 24.46 mmol) PPh₂Cl (11.12 g, 50.4 mmol) was added dropwise and the mixture refluxed for 2 hours. The reaction was allowed to cool to room temperature during which time a white precipitate was formed. Addition of diethyl ether (50 cm³) produced further precipitation.

The supernatant was removed via cannula and the residue washed with diethyl ether (4×50 cm³) and dried in vacuo to afford white microcrystals of (Ph₂P)N(H)CO(H)N(PPh₂) (6.29 g, 14.67 mmol).

EXAMPLE 3

[Pd{(Ph₂P)N(Me)CO(Ph)N(PPh₂)}(PhCN)₂][BF₄]₂ was prepared as follows:

A CH₂Cl₂ solution (20 cm³) of (Ph₂P)N(Me)CO(Ph)N(PPh₂) (0.50 g, 0.970 mmol), as prepared in Example 1, was added to a solution of [Pd(COD)Cl₂] (0.277 g, 0.970 mmol) in the same solvent (20 cm³) via cannula and stirred for one hour. The solvent was removed in vacuo, the residue washed with diethyl ether and dried. The product [Pd{(Ph₂P)N(Me)CO(Ph)N(PPh₂)}Cl₂] was then dissolved in CH₂Cl₂ and added to a second CH₂Cl₂ solution containing AgBF₄ (0.314 g, 1.940 mmol) and PhCN (1.0 cm³, 9.70 mmol) and stirred for one hour. This resulted in the formation of a AgCl precipitate which was separated from the supernatant via filter cannula. The volume of solution was reduced in vacuo to ca 10 cm³ and diethyl ether added (30 cm³) to precipitate pale yellow microcrystals of [Pd{(Ph₂P)N(Me)CO(Ph)-N(PPh₂)}(PhCN)₂][BF₄]₂ (0.486 g, 0.485 mmol).

EXAMPLE 4

[Pd{(Ph₂P)N(H)CO(H)N(PPh₂)}(MeCN)₂][BF₄]₂ was prepared using substantially the same procedure to that detailed in Example 3 except that (Ph₂P)N(F)CO(H)N(PPh₂), as prepared in Example 2, was used instead of (Ph₂P)N(Me)CO(Ph)N(PPh₂) and MeCN was used instead of PhCN.

EXAMPLE 5

A carbon monoxide/ethene copolymer was prepared as follows:

CH₂Cl₂ (110 cm³) was charged to a 300 cm³ autoclave under nitrogen. The autoclave contents were then pressurised to 30 bar G with a 1:1 mixture of carbon monoxide and ethene and heated to 70° C. A solution of B(C₆F₅)₃ (0.161 g, 0.310 mmol) in CH₂Cl₂ (10 cm³) was introduced, followed by a CH₂Cl₂ solution (10 cm³) containing [Pd(Ph₂P)N(Me)CO(Ph)N(PPh₂)(PhCN)₂][BF₄]₂ (0.015 g 0.016 mmol) prepared as in example 2. The pressure was adjusted to 50 bar G by the addition of 1:1 carbon monoxide/ethene and this pressure was maintained by the addition of the aforementioned gas mixture on demand. After 4 hours the pressure was released and the reaction was cooled to room temperature. The polymer was collected by filtration and dried under reduced pressure. 6.66 g of copolymer was obtained.

We claim:

1. A catalyst composition prepared by reacting together:
   (a) a source of a Group VIII metal,
   (b) a bidentate phosphine ligand having at least two phosphorous atoms joined by a bridging group of the formula —NR²(CX)NR² where X=O, S or Se, each R² is the same or different and is a hydrogen or hydrocarbyl group, and
   (c) a promoter.

2. A catalyst composition as claimed in claim 1 wherein the Group VIII metal is palladium.

3. A catalyst composition as claimed in claim 1 wherein R² is independently a hydrogen, or a C₁ to C₆ alkyl group.

4. A catalyst composition as claimed in claim 3 wherein each R² group is independently hydrogen, methyl, ethyl, phenyl or o methoxy phenyl.

5. A catalyst composition as claimed in claim 1 wherein the promoter is a source of a weakly-coordinating or non-coordinating anion.

6. A catalyst composition as claimed in claim 1 wherein the promoter is a boron hydrocarbyl compound.

7. A catalyst composition as claimed in claim 6 wherein the boron hydrocarbyl compound is a compound of the formula BXYZ where XY and Z are each independently a monovalent hydrocarbyl group.

8. A catalyst composition as claimed in claim 1 which the promoter is an aluminoxane.

9. A process for preparing polyketones comprising contacting carbon monoxide and at least one olefin in the presence of a catalyst composition as claimed in claim 1.

* * * * *